United States Patent
Stewart et al.

(10) Patent No.: US 6,659,981 B2
(45) Date of Patent: Dec. 9, 2003

(54) MEDICAL DEVICE DELIVERY CATHETER WITH DISTAL LOCATOR

(75) Inventors: Mark T. Stewart, Lino Lakes, MN (US); James R. Skarda, Lake Elmo, MN (US); Brian L. Dukart, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 285 days.

(21) Appl. No.: 09/733,406

(22) Filed: Dec. 8, 2000

(65) Prior Publication Data

US 2002/0072710 A1 Jun. 13, 2002

(51) Int. Cl.$^7$ ............................................... A61M 5/178
(52) U.S. Cl. ............................................... 604/164.02
(58) Field of Search ........................ 128/786; 600/585, 600/486; 604/96, 4, 158; 606/213

(56) References Cited

U.S. PATENT DOCUMENTS

| | | | |
|---|---|---|---|
| D272,651 S | | 2/1984 | Mahurkar |
| 4,602,645 A | * | 7/1986 | Barrington et al. .......... 128/786 |
| 4,643,711 A | * | 2/1987 | Bates ............................ 604/4 |
| 4,692,141 A | | 9/1987 | Mahurkar |
| 4,772,268 A | | 9/1988 | Bates |
| 4,808,155 A | | 2/1989 | Mahurkar |
| 5,195,962 A | | 3/1993 | Martin et al. |
| 5,263,493 A | | 11/1993 | Avitall |
| 5,334,159 A | * | 8/1994 | Turkel ......................... 604/158 |
| 5,374,245 A | | 12/1994 | Mahurkar |
| 5,382,238 A | | 1/1995 | Abrahamson et al. |
| 5,395,332 A | * | 3/1995 | Ressemann et al. .......... 604/96 |
| 5,405,320 A | | 4/1995 | Twardowski et al. |
| 5,451,206 A | | 9/1995 | Young |
| 5,456,680 A | | 10/1995 | Taylor et al. |
| 5,486,159 A | | 1/1996 | Mahurkar |
| 5,509,897 A | | 4/1996 | Twardowski et al. |
| 5,540,236 A | | 7/1996 | Ginn |
| 5,569,182 A | | 10/1996 | Twardowski et al. |
| 5,571,087 A | | 11/1996 | Ressemann et al. |
| 5,730,741 A | | 3/1998 | Horzewski et al. |
| 5,807,311 A | | 9/1998 | Palestrant |
| 5,830,196 A | | 11/1998 | Hicks |
| 5,879,295 A | | 3/1999 | Li et al. |
| 5,904,657 A | | 5/1999 | Unsworth et al. |
| 5,921,958 A | | 7/1999 | Ressemann et al. |
| 5,938,694 A | | 8/1999 | Jaraczewski et al. |
| 6,001,079 A | | 12/1999 | Pourchez |
| 6,117,128 A | | 9/2000 | Gregory |
| 6,120,500 A | | 9/2000 | Bednarek et al. |
| 6,132,390 A | * | 10/2000 | Cookston et al. ............ 600/585 |
| 6,193,670 B1 | * | 2/2001 | Van Tassel et al. .......... 600/486 |
| 6,368,341 B1 | * | 4/2002 | Abrahamson ................ 606/213 |
| 6,371,974 B1 | * | 4/2002 | Brenneman et al. ......... 606/213 |

* cited by examiner

*Primary Examiner*—Henry Bennett
*Assistant Examiner*—Sabrina Dagostino
(74) *Attorney, Agent, or Firm*—Girma Wolde-Michael; Daniel G. Chapik; Michael C. Soldner (57) ABSTRACT

A delivery catheter for delivering an intra-bodily medical device to an internal bodily site. The delivery catheter includes an elongated shaft defining a proximal section and a distal section. A delivery lumen is formed by the shaft, extending from the proximal section and terminating at an opening formed proximal the distal section. Finally, a locator is formed by the distal section, and is configured to locate a target site. In one preferred embodiment, the locator is elongated, having a diameter less than that of a remainder of the shaft. In another preferred embodiment, the delivery catheter includes a steering device capable of effectuating a bend both proximal and distal the opening for steering the locator to a target site.

16 Claims, 8 Drawing Sheets

MEDICAL DEVICE DELIVERY CATHETER WITH DISTAL LOCATOR

CROSS-REFERENCE TO RELATED APPLICATIONS

This application is related to U.S. patent application Ser. No. 09/733,356, entitled "Ablation Catheter Assembly and Method for Isolating a Pulmonary Vein" filed on even day herewith, assigned to the same assignee, and incorporated herein by reference thereto.

BACKGROUND OF THE INVENTION

The present invention relates to a delivery catheter for guiding an elongated medical device to an internal bodily target site. More particularly, it relates to a delivery catheter forming a distal locator for locating the target site prior to deployment of an intra-bodily medical device.

A wide variety of medical procedures are performed at or within internal bodily vessels, channels, canals, or chambers. Due to the particular procedure and/or to minimize patient trauma, oftentimes the medical device useful for performing part or all of the procedure is introduced through a small incision into the bodily vessel, channel, canal, or chamber in question; or into a bodily vessel, channel, canal, or chamber that is otherwise connected to the site of interest (or target site), and then guided through that vessel to the target site. These types of medical devices are referred to herein generally as "intra-bodily medical devices". For example, angioplasty procedures used to reduce arterial build-up include introducing a balloon-carrying catheter into a body vessel, such as a coronary artery, and maneuvering the catheter through the vessel to the target site. Similarly, one treatment of cardiac arrhythmia includes directing an ablation catheter through the inferior vena cava into the right atrium through a puncture in the interarterial septum and into the left atrium at which electrical isolation of a particular pulmonary vein can be achieved. A number of other medical procedures employ these same general protocols.

Regardless of the exact medical procedure, construction and operation of the requisite intra-bodily medical device typically requires that a separate guide device be employed to direct a distal segment (at which the operational portion of the intra-bodily medical device is typically located) to the target site. In other words, the particular intra-bodily medical device may not have sufficient rigidity to be easily advanced through body vessels, channels, canals, chambers, etc., and/or the distal segment might damage bodily tissue if left exposed during deployment to the target site. Thus, a guide catheter or sheath that coaxially maintains the intra-bodily medical device is normally employed to proficiently deliver the intra-bodily medical device, and in particular the distal segment thereof, to the target site. Following delivery of the guide catheter or sheath to the target site, the intra-bodily medical device is advanced distally or deployed to the target site through the guide catheter or sheath.

In addition, it is often times necessary to accurately locate the target site to ensure proper positioning of the distal end of intra-bodily medical device following deployment from the guide catheter or sheath. In this regard, the standard technique for locating a particular internal bodily site is use of a thin guide wire. The guide wire may be slidably disposed within a lumen formed by the intra-bodily medical device, or may be maintained by the guide catheter or sheath. In either case, the guide wire is relatively rigid and is "steered" by the surgeon to locate the target site. Once located, the intra-bodily medical device can then be deployed and accurately positioned.

While universally accepted, use of a guide wire to assist in locating a target site does have potential drawbacks. For example, because the guide wire is a component apart from the intra-bodily medical device and guide catheter or sheath, the opportunity for one of these components interfering with movement and/or operation of the other components is raised. Additionally, though guide wires are relative stiff, it is often times difficult to maneuver the distal end thereof to a desired location, especially at increased guide wire lengths and/or within relative confined areas.

A wide variety of intra-bodily medical devices are used to access and perform medical procedures on internal bodily sites. To this end, the accepted protocol of providing a separate guide body or sheath to deliver the intra-bodily medical device to the target site, as well as a separate guide wire for locating the target site is less than optimal. Therefore, a need exists for a unitary delivery catheter having a locator configured to assist in locating a target site.

SUMMARY OF THE INVENTION

One aspect of the present invention relates to a delivery catheter for delivering an intra-bodily medical device to an internal bodily site. The delivery catheter includes an elongated shaft defining a proximal section and a distal section. A delivery lumen is formed by the shaft, extending from the proximal section and terminating at an opening formed proximal the distal section. Finally, a locator is formed by the distal section, and is configured to locate a target site. In one preferred embodiment, the locator is elongated, having a diameter less than that of a remainder of the shaft. In another preferred embodiment, the delivery catheter includes a steering device capable of effectuating a bend both proximal and distal the opening for steering the locator to a target site.

Another aspect of the present invention relates to a catheter assembly for performing a medical procedure within an internal bodily site. The catheter assembly includes an intra-bodily medical device and a delivery catheter. The intra-bodily medical device has a distal end and is configured to perform a medical procedure. In this regard, a wide variety of intra-bodily medical devices are available, ranging from ablation catheter devices to angioplasty, fiber optics, basket catheters, etc. Regardless, the delivery catheter comprises an elongated shaft defining a proximal section and a distal section. A delivery lumen is formed by the shaft, extending from the proximal section and terminating at an opening proximal the distal section. In this regard, the delivery lumen is sized to slidably receive the intra-bodily medical device. Finally, a locator is formed by the distal section and is configured to locate a target site. With this configuration in mind, the intra-bodily medical device is slidably disposed within the delivery lumen, and is moveable between a retracted position in which the distal end of the intra-bodily medical device is proximal of the opening and a deployed position in which the distal end is distal the opening. During use, the delivery catheter guides the intra-bodily medical device, in the retracted position, to a target site. The locator is employed to locate the target site. Finally, the intra-bodily medical device is maneuvered to the deployed position to perform a medical procedure.

Yet another aspect of the present invention relates to a method of deploying an intra-bodily medical device to an internal bodily target site. The method includes providing a delivery catheter including an elongated shaft having a proximal section, an intermediate section, a distal locator, and a delivery lumen. The delivery lumen extends from the proximal section to an opening formed proximal the distal locator. An intra-bodily medical device having a distal end is also provided. The delivery catheter is deployed so as to position the distal locator adjacent the target site. The target site is located with the distal locator. The elongated medical device is advanced in a distal fashion within the delivery lumen such that the distal end is deployed distally beyond the opening for performing a medical procedure on the target site. Finally, the intra-bodily medical device is retracted in a proximal fashion within the delivery lumen such that the distal end is retracted proximal the opening.

DESCRIPTION OF THE PREFERRED EMBODIMENTS

Figure 1:
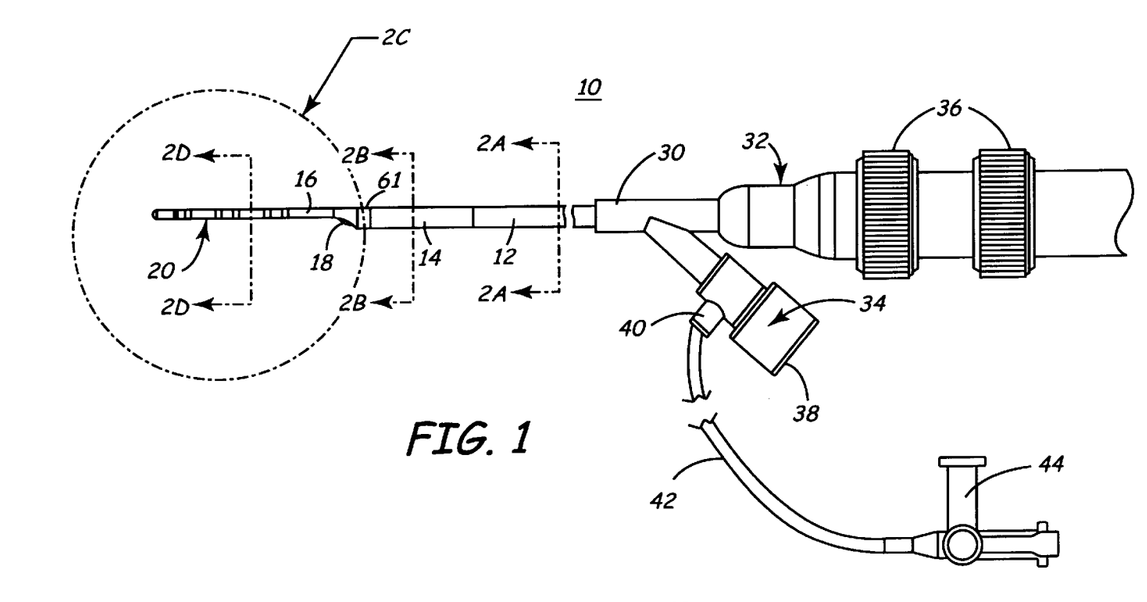
FIG. 1 is a side view of a delivery catheter in accordance with the present invention.

One preferred embodiment of a delivery catheter 10 in accordance with the present invention is shown in FIG. 1. The delivery catheter 10 includes a proximal section 12, an intermediate section 14, and a distal section 16. The intermediate section 14 extends from the proximal section 12 and terminates at an opening 18. The distal section 16 extends from the intermediate section 14 distal the opening 18. As described in greater detail below, the distal section 16 forms a locator 20. As a point of reference, in the preferred embodiment of FIG. 1, the locator 20 is defined by an entirety of the distal section 16. Regardless, the delivery catheter 10 is configured for delivering an intra-bodily medical device (not shown) to an internal bodily site, and thus forms a delivery lumen (not shown) extending from the proximal section 12 to the opening 18. In this regard, and as described in greater detail below, the delivery catheter 10 is preferably steerable both proximal and distal the opening 18.

In light of the preferred steerable attribute of the delivery catheter 10, the proximal section 12 preferably includes a Y-connector 30 coupled to a handpiece 32 and a hemostatic valve 34. The handpiece 32 is of a type known in the art and provides control devices 36, the operation of which (i.e., rotation) effectuates desired bending of the delivery catheter 10 via pull wires (not shown) described in greater detail below. The hemostatic valve 34 is fluidly connected to the delivery lumen (not shown) and preferably forms a first port 38 and a second port 40. The first port 38 is available for receiving and directing an intra-bodily medical device or other elongated body (not shown) to the delivery lumen. Further, the second port 40 is also fluidly connected to the delivery lumen, and is available for delivering a fluid to the delivery lumen. For example, in one preferred embodiment, a tube 42 extends from the second port 40 to a stop cock valve 44. as is known in the art, the hemostatic valve 34 in conjunction with the stop cock valve 44 allows flushing of a liquid, such as saline, through the delivery lumen, while preventing a back flow of other liquids, such as blood.

Figure 2A:
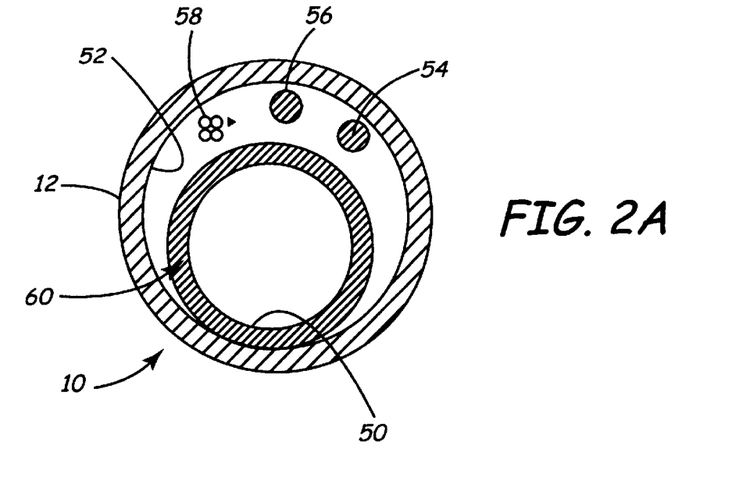
FIG. 2A is an enlarged, cross-sectional view of the delivery catheter of FIG. 1 along the line 2A—2A.

With further reference to FIG. 2A, the proximal section 12 forms the delivery lumen 50 described above. In addition, the proximal section 12 forms a passage 52 surrounding the delivery lumen 50 and maintaining, as depicted in FIG. 2A, a first pull wire 54, a second pull wire 56 and a cluster of electrode wires 58. In one preferred embodiment, the delivery lumen 50 is defined by a tube 60 co-axially disposed within the passage 52. Alternatively, the proximal section 12 can be configured to integrally form the delivery lumen 50. The first pull wire 54 extends from the handpiece 32 to the intermediate section 14 for effectuating steering or bending of the delivery catheter 10 proximal the opening 18. The second pull wire 56 extends from the handpiece 32 to the distal section 16 for effectuating steering or bending of the delivery catheter 10 distal the opening 18. Finally, the cluster of electrode wires 58 are electrically connected to an auxiliary energy source (not shown) for energizing various electrodes associated with the delivery catheter 10, as described in greater detail below.

The proximal section 12 is preferably formed of a reinforced, braided material such as a tubular shaft constructed of "Ultem" polyamide, or other high temperature polymer covered with a reinforcing braid wire or high strength filament and jacketed by a flexible polymer such as nylon, polyurethane, or "PEBAX"™. With this preferred material, the proximal section 12 exhibits enhanced torqueability, such that a user can more easily steer or guide the delivery catheter 10 to a target site.

Figure 2B:
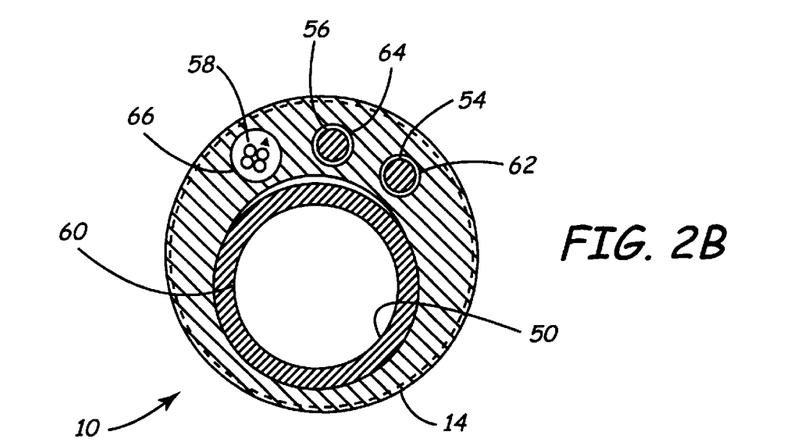
FIG. 2B is an enlarged, cross-sectional view of the delivery catheter of FIG. 1 along the line 2B—2B.

The intermediate section 14 forms the opening 18 and preferably maintains an electrode 61. With additional reference to FIG. 2B, the intermediate section 14 defines first, second, and third lumens 62–66, in addition to the delivery lumen 50. The delivery lumen 50 is preferably defined by the tube 60 otherwise carried within the intermediate section 14. Alternatively, the delivery lumen 50 can be integrally formed by the intermediate section 14. Once again, the delivery lumen 50 is available to slidably maintain an intra-bodily medical device (not shown) or other body, and terminates at the opening 18. The first pull wire 54 extends through the first lumen 62 and is secured to the intermediate section 14 adjacent the opening 18. The second pull wire 56 extends through the second lumen 64. Finally, the cluster of electrode wires 58 are maintained within the third lumen 66.

The electrode 61 is preferably a band electrode electrically connected to one or more of the cluster of electrode wires 58. With this configuration, the electrode 61 is available as a mapping electrode. Notably, however, the electrode 61 is not a necessary element of the delivery catheter 10.

The intermediate section 14 is preferably formed of a material different from that of the proximal section 12. More particularly, unlike the preferably reinforced, torqueable composition of the proximal section 12, the intermediate section 14 is preferably comprised of a softer material such as nylon, polyurethane, or "PEBAX"™. With this configuration, the intermediate section 14 is highly amenable to bending via tensioning of the first pull wire 54. To this end, a length of the intermediate section 14 (i.e., longitudinal distance proximal the opening 18) dictates the focal point at which bending of the intermediate section 14 occurs, as well as an available bend radius. In a preferred embodiment, the intermediate section 14 has a longitudinal length in the range of 5–24 cm, more preferably 15 cm.

Figure 2C:
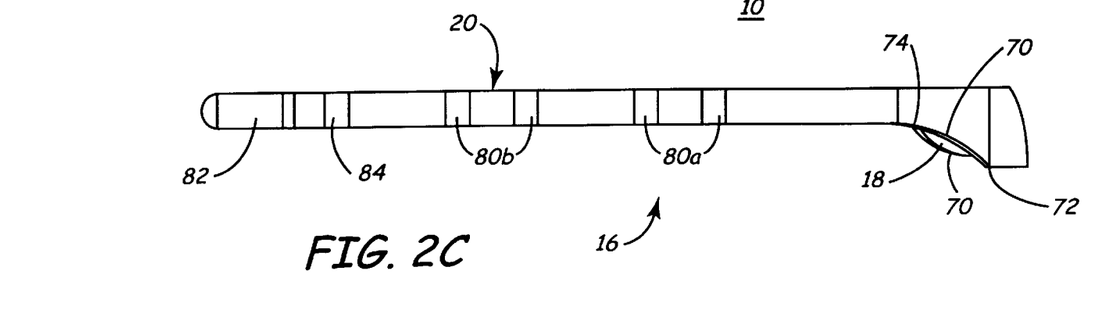
FIG. 2C is an enlarged, side view of a distal portion of the delivery catheter of FIG. 1.

The opening 18 is shown more clearly in FIG. 2C. The opening is defined by an outer edge 70 extending from a proximal end 72 to a distal end 74. In a preferred embodiment, the edge 70 is rounded or curved so as to minimize tissue damage as the delivery catheter 10 is passed through bodily lumens, for example veins. Alternatively, however, the opening 18 may assume a wide variety of other forms. Further, as described below, a rounded-tip dilator (not shown) is preferably extended into and/or through the opening 18 to further minimize the opportunity for tissue damage during deployment.

Figure 2D:
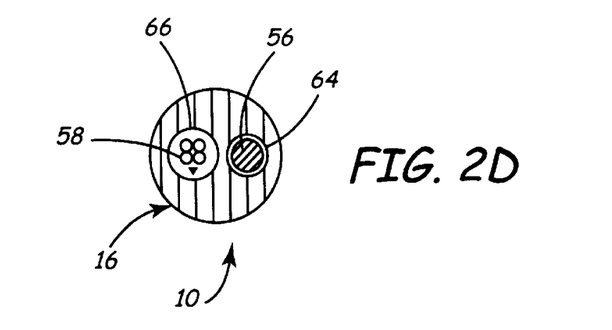
FIG. 2D is an enlarged, cross-sectional view of the delivery catheter of FIG. 1 along the line 2D—2D.

The distal section 16 extends distally beyond the opening 18, forming the locator 20. In one preferred embodiment, the locator 20 extends the entire length of the distal section 16, although the locator 20 may have a length less than that of the distal section 16. Further, in one preferred embodiment, the distal section 16 includes electrode pairs 80a and 80b and terminates at a tip 82 that, in one preferred embodiment, incorporates a thermocouple and serves as an electrode pair with an electrode 84. With additional reference to FIG. 2D, the distal section 16, including the locator 20, defines the second lumen 64, maintaining the second pull wire 56, and the third lumen 66, maintaining the cluster of electrode wires 58. The second pull wire 56 is attached to the locator 20 adjacent the tip 82. The cluster of electrode wires 58 are connected to the pairs of electrodes 80a and 80b, as well as the tip 82 and the electrode 84. With this configuration, the electrode pairs 80a and 80b, as well as the tip 82 and the electrode 84, are available for mapping and/or ablation functions. The electrodes 80a, 80b, 82, 84 are preferably band electrodes, although other constructions are equally acceptable. Even further, one or more of the electrodes 80a, 80b, 82, 84 can be eliminated.

The distal section 16, including the locator 20, is preferably formed from a soft material similar to the intermediate region 14, preferably nylon, polyurethane, or "PEBAX"™. With this configuration, the locator 20 is bendable or steerable via tensioning of the second pull wire 56. As is illustrated best in FIG. 1, the locator 20 is preferably formed to an outer diameter less than that of the intermediate section 14 and the proximal section 12. In one preferred embodiment, the locator 20 has an outer diameter in the range of 5–7 French, more preferably 6 French, whereas the intermediate section 14 has a diameter in the range of approximately 10–13 French. Further, the locator 20 extends an appreciable distance distal the opening 18 so as to provide sufficient surface area for locating a target site. With this in mind, in one preferred embodiment, the locator 20 has a length in the range of 5–20 cm, more preferably 15 cm.

Figure 3:
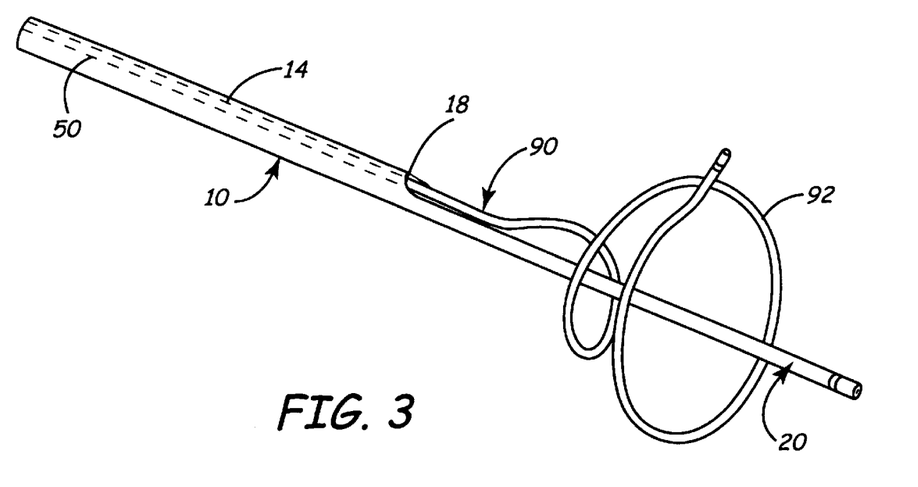
FIG. 3 is a perspective view of a catheter assembly including the delivery catheter of FIG. 1 in conjunction with an elongated medical device.

The above-described delivery catheter 10 is available to deliver a wide variety of different intra-bodily medical devices to an internal bodily site. For example, FIG. 3 depicts the delivery catheter 10 in conjunction with an ablation catheter 90 useful for ablating an enclosed pattern about a pulmonary vein ostium for treatment of cardiac arrhythmia. The ablation catheter 90 includes a distal region 92 and is slidably disposed within the delivery lumen 50 otherwise formed by the delivery catheter 10. Use and operation of the delivery catheter 10 is independent of the construction and operation of the ablation catheter 90, therefore, the ablation catheter 90 need not be described in detail. In general terms, the distal region 92 of the ablation catheter 90 is configured to ablate contacted tissue, such as by activation of one or more electrodes (not shown). Regardless, the ablation catheter 90 is moveable within the delivery lumen 50 between a deployed position (shown in FIG. 3) in which the distal region 92 is advanced distal the opening 18, and a retracted position (not shown) in which the distal region 92 is retracted proximal the opening 18.

Figure 4:
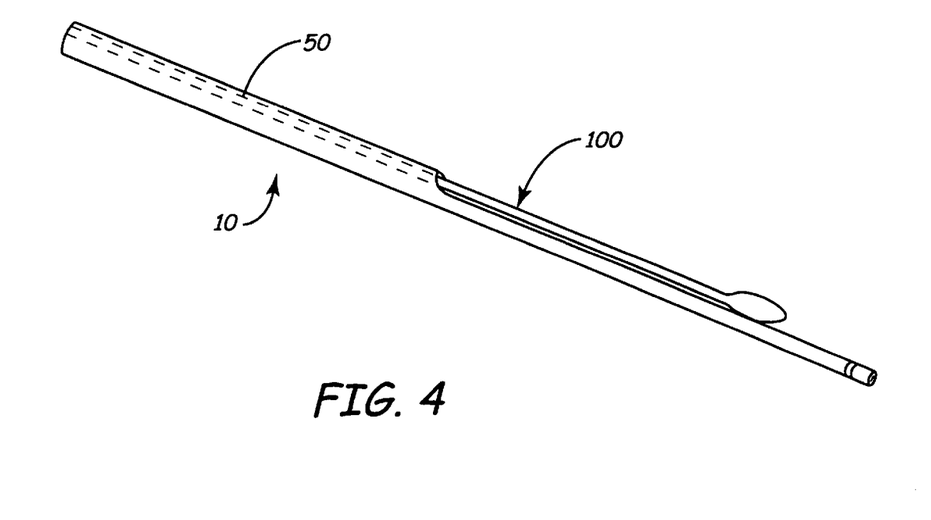
FIG. 4 is a side, perspective view of a catheter assembly including the delivery catheter of FIG. 1 and an alternative elongated medical device.

The delivery catheter 10 can be used with a wide variety of other intra-bodily medical devices different from the ablation catheter 90. For example, FIG. 4 depicts the delivery catheter 10 in conjunction with a balloon catheter 100. Once again, the balloon catheter 100 is slidably disposed within the delivery lumen 50, movable between a deployed position (shown in FIG. 4) and a retracted position relative to the opening 18. As is further exemplified by the example of FIG. 4, a central axis of the locator 20 is preferably parallel with a central axis of the delivery lumen 50. With this preferred configuration, the intra-bodily medical device (e.g., the balloon catheter 100) is deployed parallel with, and in close proximity to, the locator 20, so that the locator 20 will more easily guide the intra-bodily medical device upon deployment thereof.

A number of other intra-bodily medical devices are equally acceptable for use with the delivery catheter 18, including intra-vascular ultrasound devices, intra-cardiac echo devices, angiographic devices, balloon angiography devices, fiber optic devices, biopsy devices, cryo-catheter devices, electrophysiology catheter devices, basket mapping catheter devices, thermal therapy balloon devices, device retrieving catheters, etc.

Figure 5A:
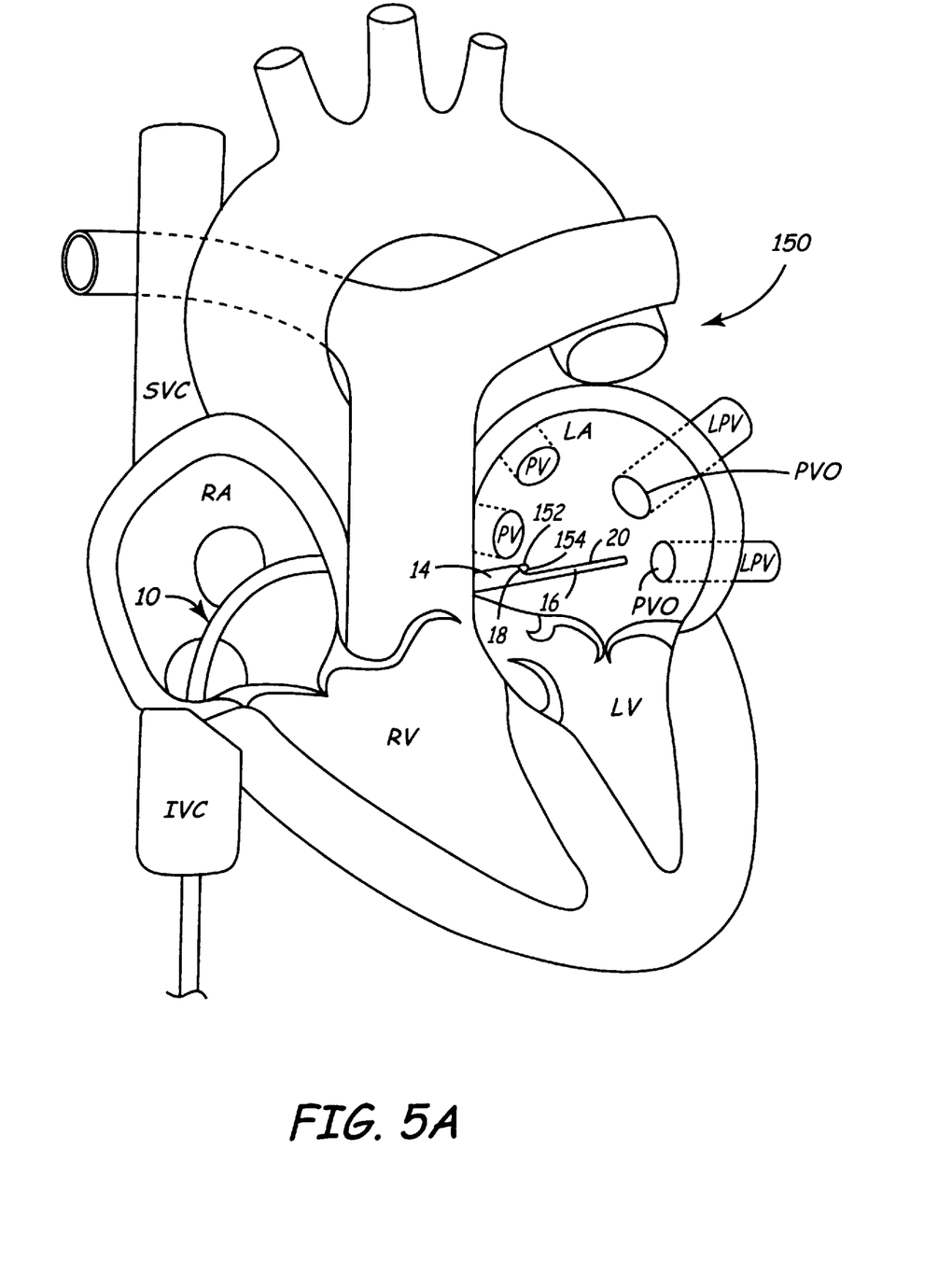
FIGS. 5A–5C illustrate deployment of an elongated medical device with the delivery catheter of FIG. 1 within a heart in accordance with the present invention.
Figure 5B:
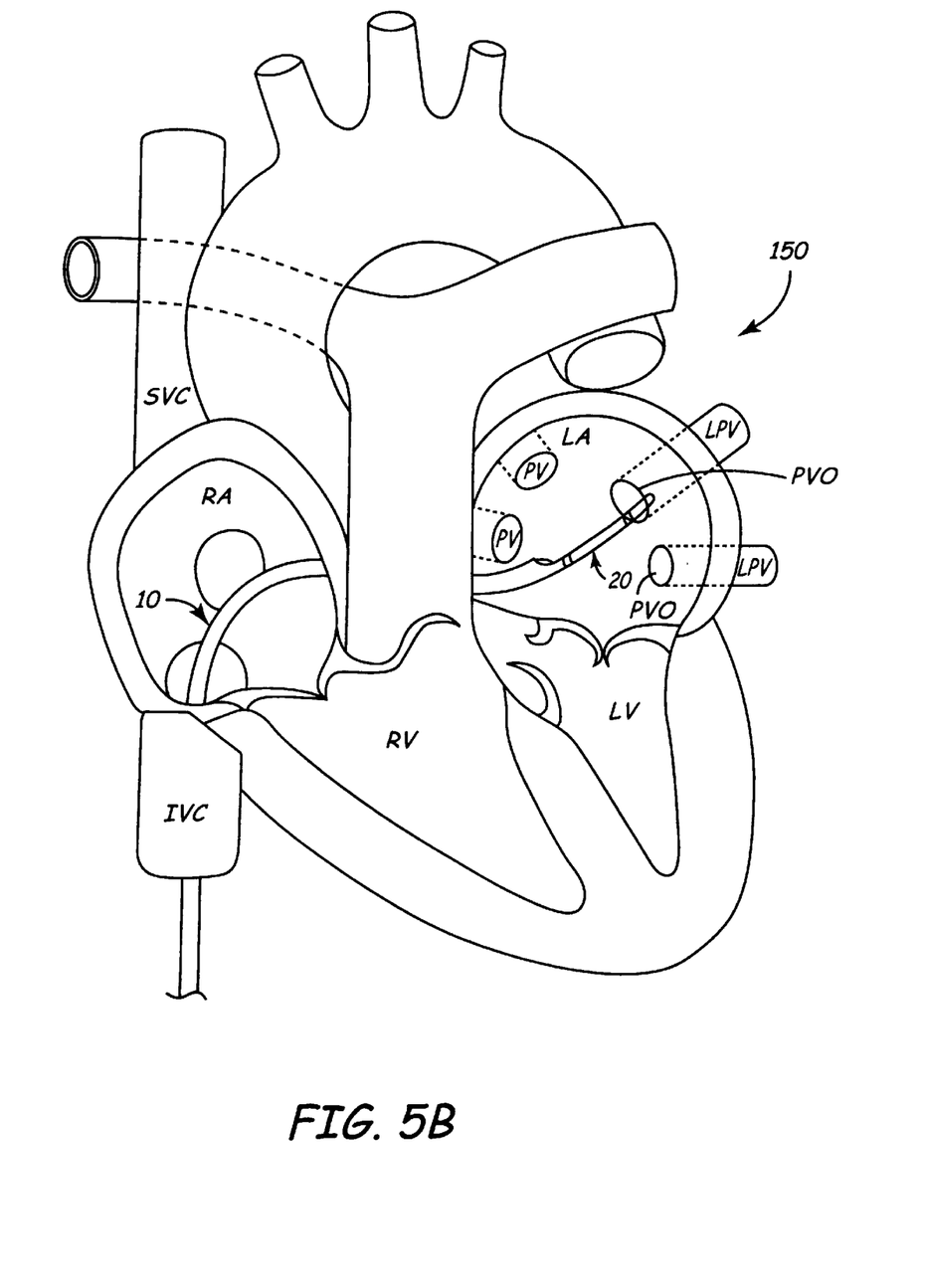
Figure 5C:
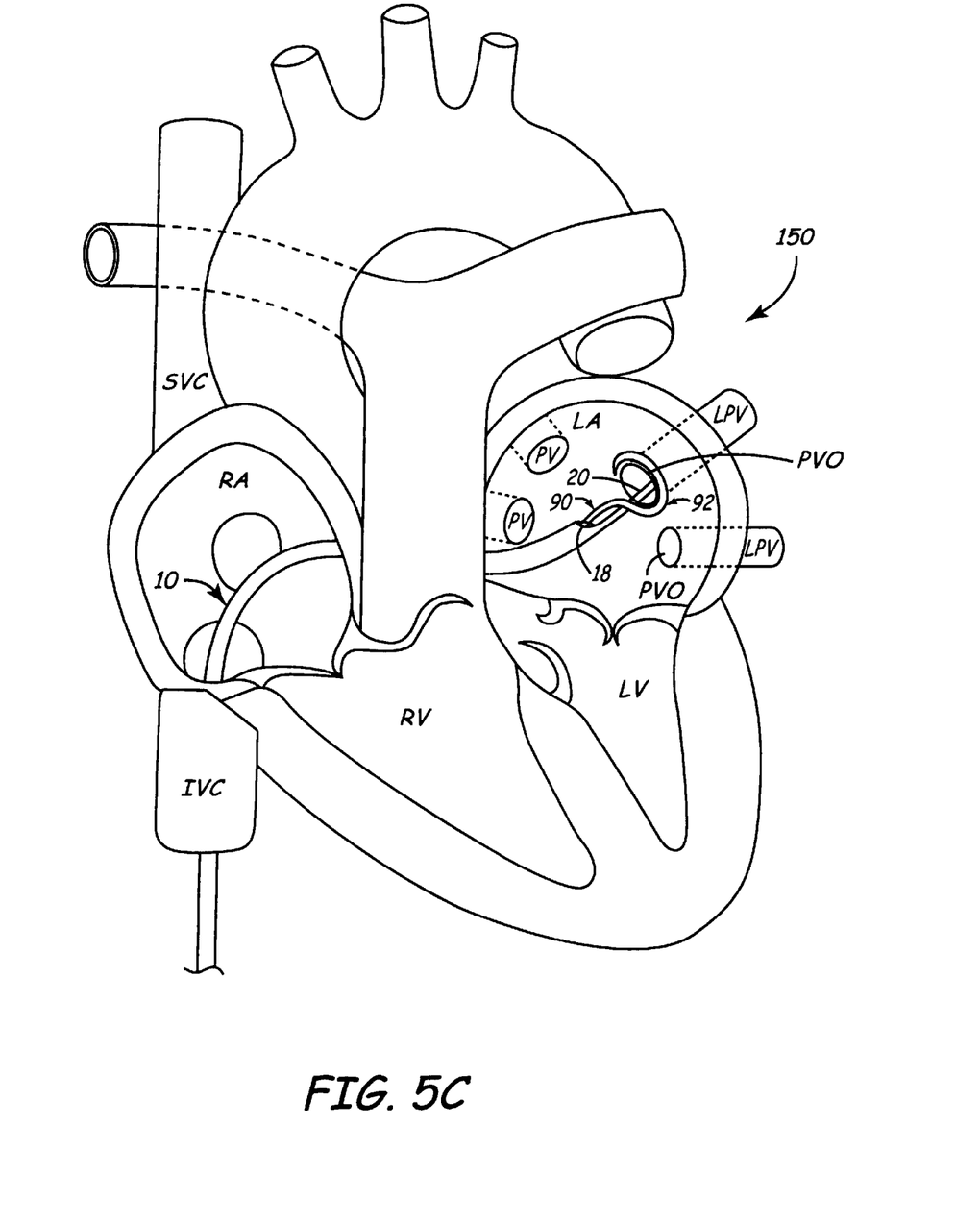

Use of the delivery catheter 10 is dependent upon the particular medical procedure to be performed, and thus the particular intra-bodily medical device carried by the delivery catheter 10. For example, where the medical procedure is heart tissue ablation for treatment of cardiac arrhythmia, an ablation catheter, such as the ablation catheter 90 depicted in FIG. 3, must be deployed within the heart. For this one specific example, FIGS. 5A–5C illustrate use of the delivery catheter 10 within a heart 150 in conjunction with an ablation catheter. As a point of reference, the heart 150 includes a right atrium RA, a left atrium LA, a right ventricle RV, and a left ventricle LV. An inferior vena cava IVC and a superior vena cava SVC lead into the right atrium RA. The right atrium RA is separated from the left atrium LA by an interarterial septum (not shown). Finally, four pulmonary veins PV extend from the left atrium LA. Each of the pulmonary veins PV forms an ostium PVO in the left atrium LA wall. During formation of the heart 150, it is possible that tissue of the left atrium LA may grow upwardly into one or more of the pulmonary veins PV. This left atrium LA tissue may spontaneously depolarize, resulting in atrial fibrillation. This malady is treatable by ablating tissue about the associated pulmonary vein ostium PVO to electrically isolate the depolarizing tissue.

As shown in FIG. 5A, electrical isolation of a pulmonary vein PV includes directing the delivery catheter 10 toward the target site (e.g., the pulmonary vein ostium in question). In particular, the distal section 16 of the delivery catheter 10 is directed through the inferior vena cava IVC, into the right atrium RA through a puncture in the interarterial septum (not shown) and into the left atrium LA. Alternatively, the introduction of the distal section 16 of the delivery catheter 10 into the right atrium RA is also suggested by passage of the distal section 16 into the right atrium RA through the superior vena cava SVC. In one preferred embodiment, prior to placement within the patient, a rounded-tip dilator 152 is slidably disposed within the delivery lumen 50 (FIG. 1), a distal end 154 of which extends at least partially out of the opening 18. By providing the dilator 152, the delivery catheter 10 can be fed through bodily lumens, such as veins, without damaging tissue at the opening 18.

Once the intermediate section 14 and the distal section 16, including the locator 20, have been guided to the general area of interest (e.g., the left atrium LA), the rounded-tip dilator 152 is removed from the delivery lumen 50, and the intra-bodily medical device, for example the ablation catheter 90, inserted therein.

The locator 20 of the delivery catheter 10 is then maneuvered to locate the target site. With respect to the one example of FIGS. 5A–5C in which an ablation pattern is to be formed about a pulmonary vein ostium PVO, the target site is the associated pulmonary vein PV. Thus, the locator 20 is directed into the pulmonary vein PV to locate the pulmonary vein ostium PVO, as shown in FIG. 5B. To this end, an available visualization device, such as a fluoroscope, can be employed to confirm placement of the locator 20 within the pulmonary vein PV. Further, the various electrodes, including the electrodes 80a, 80b, 82 and/or 84 provided along the locator 20 can be selectively activated and their signals reviewed to further confirm placement of the locator 20 within the pulmonary vein PV, as well as to evaluate electrical activity at the target site.

Once the target site has been located with the locator 20, the ablation catheter 90 is advanced to a deployed position in which the distal region 92 extends distal the opening 18. The ablation catheter 90 is further advanced so as to position the distal region 92 against the target site (e.g., about the pulmonary vein ostium PVO), as shown in FIG. 5C. In this regard, the locator 20 serves as a guide to facilitate proper positioning of the distal region 92, as well as anchoring the delivery catheter 10, and thus the ablation catheter 90, relative to the target site. While with the one specific example provided in FIGS. 5A–5C, the distal region 92 of the ablation catheter 90 forms a helix that engages, and is thus directly guided by, the locator 20, such an arrangement is not required. In other words, the locator 20 need not specifically contact or otherwise engage the intra-bodily medical device to generally direct the distal region (such as the distal region 92) to the target site. Additionally it is not required that the locator 20 locate the target site prior to deployment of the intra-bodily medical device (e.g., the ablation catheter 90). That is to say, the intra-bodily medical device (e.g., the ablation catheter 90) can be deployed first, and then the target site be located with the locator 20.

Once properly positioned, the intra-bodily medical device, such as the ablation catheter 90, is operated to perform the desired medical procedure. For example, with reference to the one specific example of FIGS. 5A–5C, the ablation catheter 90 is operated to ablate a continuous pattern about the pulmonary vein ostium PVO, thereby electrically isolating the pulmonary vein PV from the heart 150. Following completion of the medical procedure, the intra-bodily medical device, such as the ablation catheter 90, is retracted within the delivery lumen 50 (FIG. 1) such that the distal region (such as the distal region 92) is no longer "exposed". The delivery catheter 10 is then removed from the patient. Alternatively, other similar medical procedures can be performed at the target site or other target sites (e.g., electrical isolation of other pulmonary vein ostia PVOs). In this regard, the intra-bodily medical device (such as the ablation catheter 90) can be repeatedly used or can be replaced by another device configured to perform a different medical procedure. In either case, the locator 20 is available for locating the target site and generally guiding the medical device into a proper position.

Once again, the medical procedure described with respect to FIGS. 5A–5C is but one procedure for which the delivery catheter 10 is applicable. Other medical procedures can be performed with the delivery catheter 10 at different internal bodily sites with entirely different intra-bodily medical devices. Regardless, the locator 20 is utilized to locate the target site generally anchor the delivery catheter 10, and guide the intra-bodily medical device in question to a proper position relative to the target site.

Figure 6:
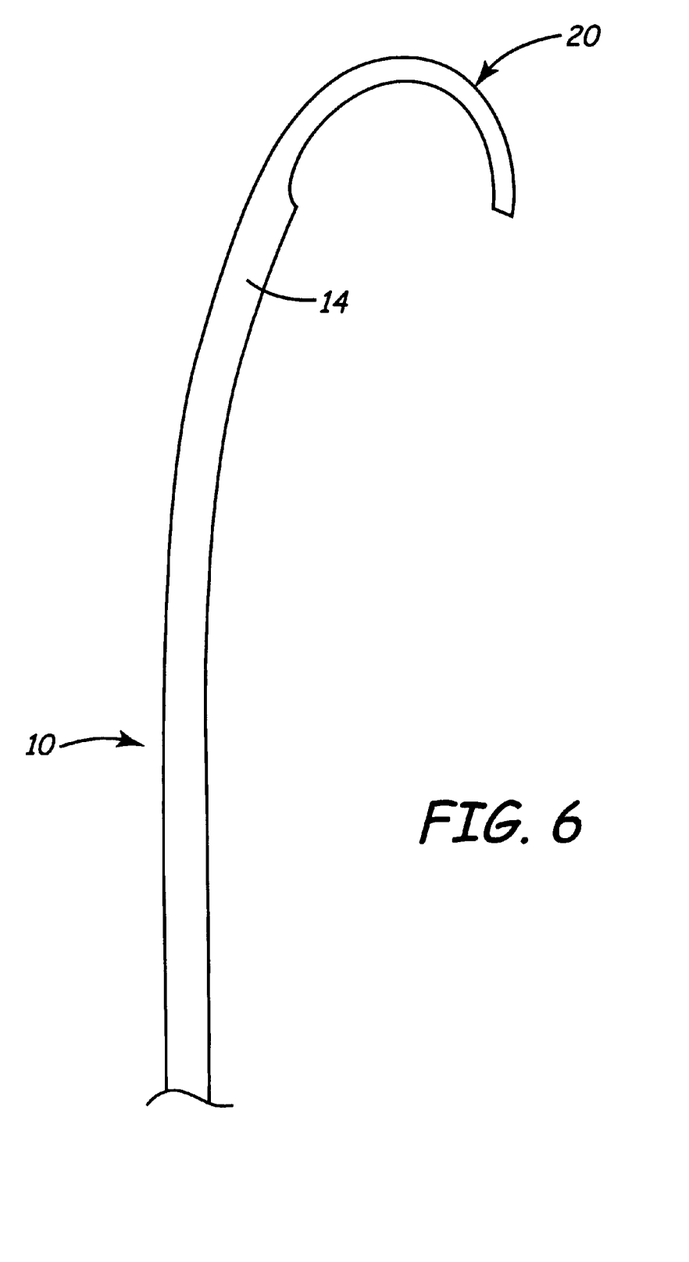
FIG. 6 is a side view of the delivery catheter of FIG. 1, illustrating steering capabilities.

Often times, the particular target site for which the delivery catheter 10 is to be deployed requires relatively radical articulation or steering of the delivery catheter 10 to properly position the locator 20. For example, with reference to the cardiac arrhythmia treatment procedure described above, following deployment into the left atrium LA via the interarterial septum, the right pulmonary veins RPVs are effectively located "behind" the locator 20, such that it is impossible to position the locator 20 within one of the right pulmonary veins RPVs by simply advancing the delivery catheter 10 forward. Instead, the delivery catheter 10 must be steered to properly position the locator 20. In this regard, FIG. 6 depicts steering capabilities of the delivery catheter 10 in accordance with one preferred embodiment. The delivery catheter 10 is preferably configured to effectuate bends both proximal and distal of the opening 18. For example, the first pull wire 54 (FIG. 2A) can be tensioned to effectuate a major bend at the intermediate section 14 (or proximal the opening 18). This "gross" bend provided proximate of the opening 18 generally positions the locator 20.

Conversely, the second pull wire 56 can be tensioned to effectuate a bend in the locator 20 (or distal the opening 18). Steering of the locator 20 provides exacting control of a position of the locator 20. As will be recognized by one of skill in the art, steering means other than pull wires can be employed to effectuate the preferred bends proximal and distal the opening 18.

The delivery catheter 10 of the present invention provides a marked improvement over previous designs. In particular, the delivery catheter combines the performance attributes of a delivery sheath and guide wire into a single, unitary device. Further, by configuring the delivery catheter to be steerable both proximal and distal the opening through which the intra-bodily medical device is deployed, rapid engagement of a target site is promoted.

Although the present invention has been described with reference to preferred embodiments, workers skilled in the art will recognize that changes can be made in form and detail without departing from the spirit and scope of the present invention. For example, the delivery catheter has been preferably described as incorporating a series of electrodes or electrode pairs along the distal section thereof. Alternatively, where a particular medical procedure does not require mapping or similar functions, the electrode or electrode pairs can be eliminated and therefore are not necessary elements.

What is claimed is:

1. A delivery catheter for delivering an intra-bodily medical device to an internal bodily site, the delivery catheter comprising:

an elongated shaft including a proximal section, an intermediate section extending from the proximal section, and a distal section extending from the intermediate section along a first central axis and forming a locator configured to locate and be positioned at a target site; and a delivery lumen, formed by the shaft, extending from the proximal section along a second central axis and terminating at an opening formed proximal the distal section, wherein the first central axis is offset from and parallel to the second central axis and the intra-bodily medical device is insertable within the delivery lumen and directed by the distal section to be positioned at the target site as the intra-bodily medical device is advanced through the delivery lumen and outward from the opening.

2. The delivery catheter of claim 1, wherein the delivery lumen is configured to slidably receive an intra-bodily medical device, and further wherein the opening is configured to allow selective deployment of at least a portion of an intra-bodily medical device relative to the opening.

3. The delivery catheter of claim 1, wherein the elongated shaft is configured such that the locator is bendable.

4. The delivery catheter of claim 3, further comprising:
locator steering means for selectively bending the locator distal the opening.

5. The delivery catheter of claim 4, wherein the locator steering means includes at least one pull wire extending from the proximal section and terminating within the distal section.

6. The delivery catheter of claim 4, wherein the locator steering means includes at least one pull wire extending from the proximal section to the intermediate section, the pull wire terminating within the intermediate section.

7. The delivery catheter of claim 3, wherein the proximal section is formed of a first material and the locator is formed of a second material, the first material being stiffer than the second material.

8. The delivery catheter of claim 3, wherein the proximal section is formed of a first material and the intermediate section is formed of a second material, the first material being stiffer than the second material.

9. The delivery catheter of claim 1, wherein the locator has a diameter less than a diameter of the intermediate section.

10. The delivery catheter of claim 1, wherein the locator has a length of at least 5 cm.

11. The delivery catheter of claim 1, wherein the opening is defined by an edge extending from a proximal end to a distal end, and further wherein the edge is curved.

12. The delivery catheter of claim 1, further comprising:
an elongated dilator forming a rounded tip, the elongated dilator being configured for selective placement within the delivery lumen such that the rounded tip selectively extends at least partially from the opening.

13. The delivery catheter of claim 1, further comprising an electrode positioned along the locator performing one of mapping, ablation, and mapping and ablation functions.

14. The delivery catheter of claim 13, further comprising a mapping electrode positioned along the intermediate section of the shaft.

15. The delivery catheter of claim 3, further comprising:
an actuating device positioned along the proximal section of the shaft;
a first pull wire extending from the actuating device to the intermediate section of the shaft effectuating bending along the intermediate section of the shaft through the actuating device; and
a second pull wire extending from the actuating device to the distal section of the shaft effectuating bending along the distal section of the shaft through the actuating device.

16. The delivery catheter of claim 14, further comprising:
an actuating device positioned along the proximal section of the shaft;
a first pull wire extending from the actuating device to the intermediate section of the shaft effectuating bending along the intermediate section of the shaft through the actuating device; and
a second pull wire extending from the actuating device to the distal section of the shaft effectuating bending along the distal section of the shaft through the actuating device.

* * * * *